United States Patent [19]

Corsi et al.

[11] Patent Number: 5,190,545
[45] Date of Patent: Mar. 2, 1993

[54] CERCLAGE WIRE POSITIONING INSERT

[75] Inventors: George M. Corsi, Aberdeen; Richard M. Brooks, West Milford; Paul J. Viola, Bogota, all of N.J.

[73] Assignee: Pfizer Hospital Products Group, Inc., New York, N.Y.

[21] Appl. No.: 750,666

[22] Filed: Aug. 27, 1991

[51] Int. Cl.$^5$ .............................................. A61B 17/58
[52] U.S. Cl. ........................................ 606/74; 606/60; 606/72
[58] Field of Search ................ 606/53, 60, 69, 72, 606/74, 86, 103; 24/16 R, 18, 272, 27, 28, 271, 279, 662, 332

[56] References Cited

U.S. PATENT DOCUMENTS

| 145,582 | 12/1873 | Miller | 24/271 UX |
|---|---|---|---|
| 580,841 | 4/1897 | Barceloux | 24/28 |
| 736,628 | 8/1903 | Priddat | 24/18 |
| 902,040 | 10/1908 | Wyckoff | 606/74 X |
| 1,282,848 | 10/1918 | Jones | 606/74 X |
| 1,950,993 | 3/1934 | Jones | 606/74 |
| 2,502,904 | 4/1950 | Tofflemire | 606/74 X |
| 3,469,573 | 9/1969 | Florio | 606/74 |
| 3,710,789 | 1/1973 | Ersek | 606/60 |
| 4,640,536 | 2/1987 | Printiss, Jr. et al. | 24/279 X |
| 4,648,159 | 3/1987 | Dougherty | 24/18 X |

FOREIGN PATENT DOCUMENTS 543126  8/1922  France ................. 606/103

Primary Examiner—Robert A. Hafer
Assistant Examiner—Sam Rimell
Attorney, Agent, or Firm—Peter C. Richardson; Lawrence C. Akers; Raymond W. Augustin

[57] ABSTRACT

A bone fracture stabilization apparatus includes a cable positioning insert for a bone plate of the type having a series of apertures therein for receiving bone screws for attaching the bone plate to the bone. The cable positioning insert has a body shaped for at least partial insertion into at least one of the apertures of the bone plate. The insert further includes a flange extending from the body for engaging either the outer or inward surface of the bone plate. A boss extends from the body in a direction away from the bone when the bone plate is mounted thereon. The boss has at least one opening and preferably two openings therein for accommodating a cerclage cable and positioning it relative to the apertures in the bone. The boss may be made of a malleable material that deforms under pressure to flatten the openings therein and capture the cable.

13 Claims, 7 Drawing Sheets

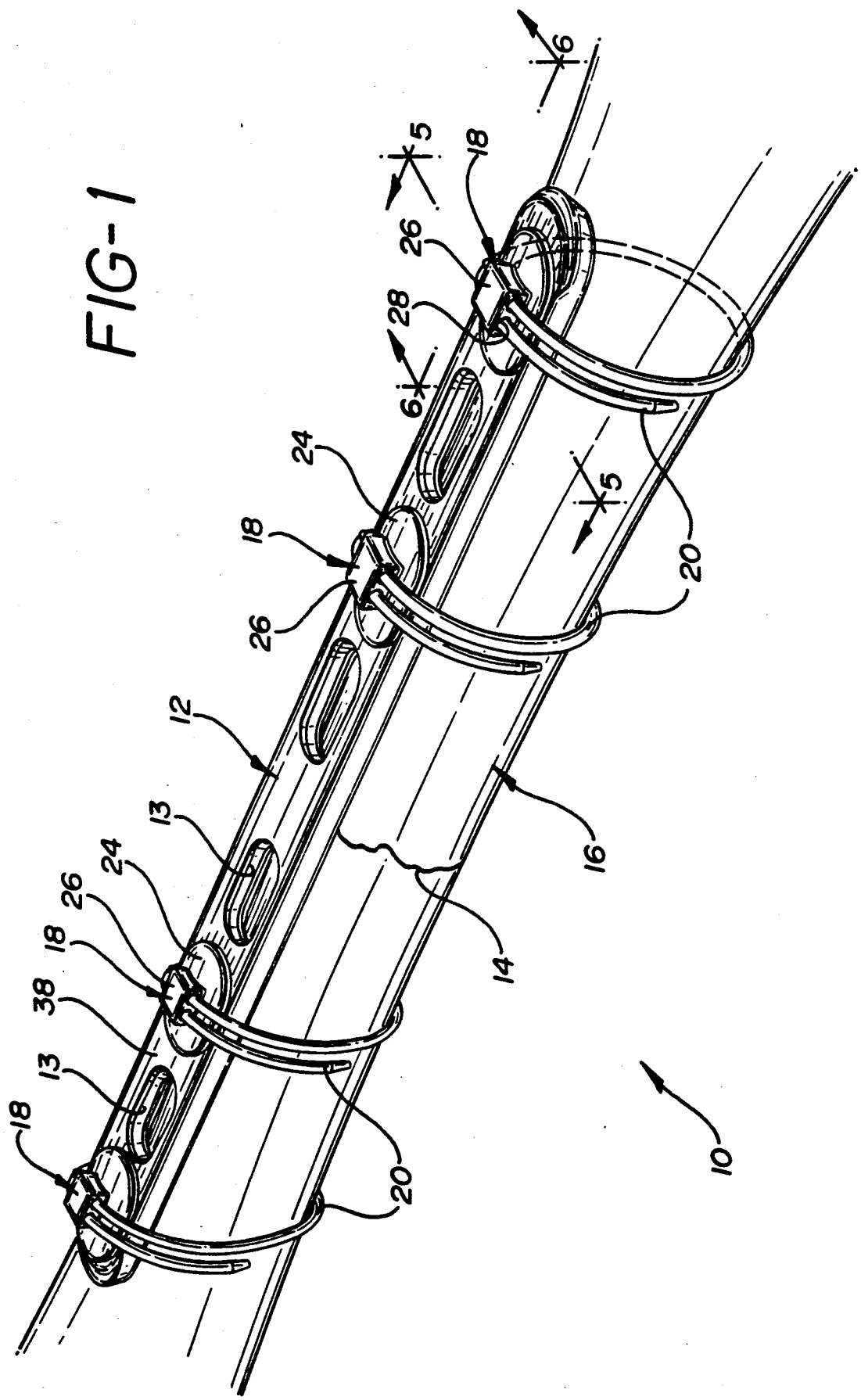

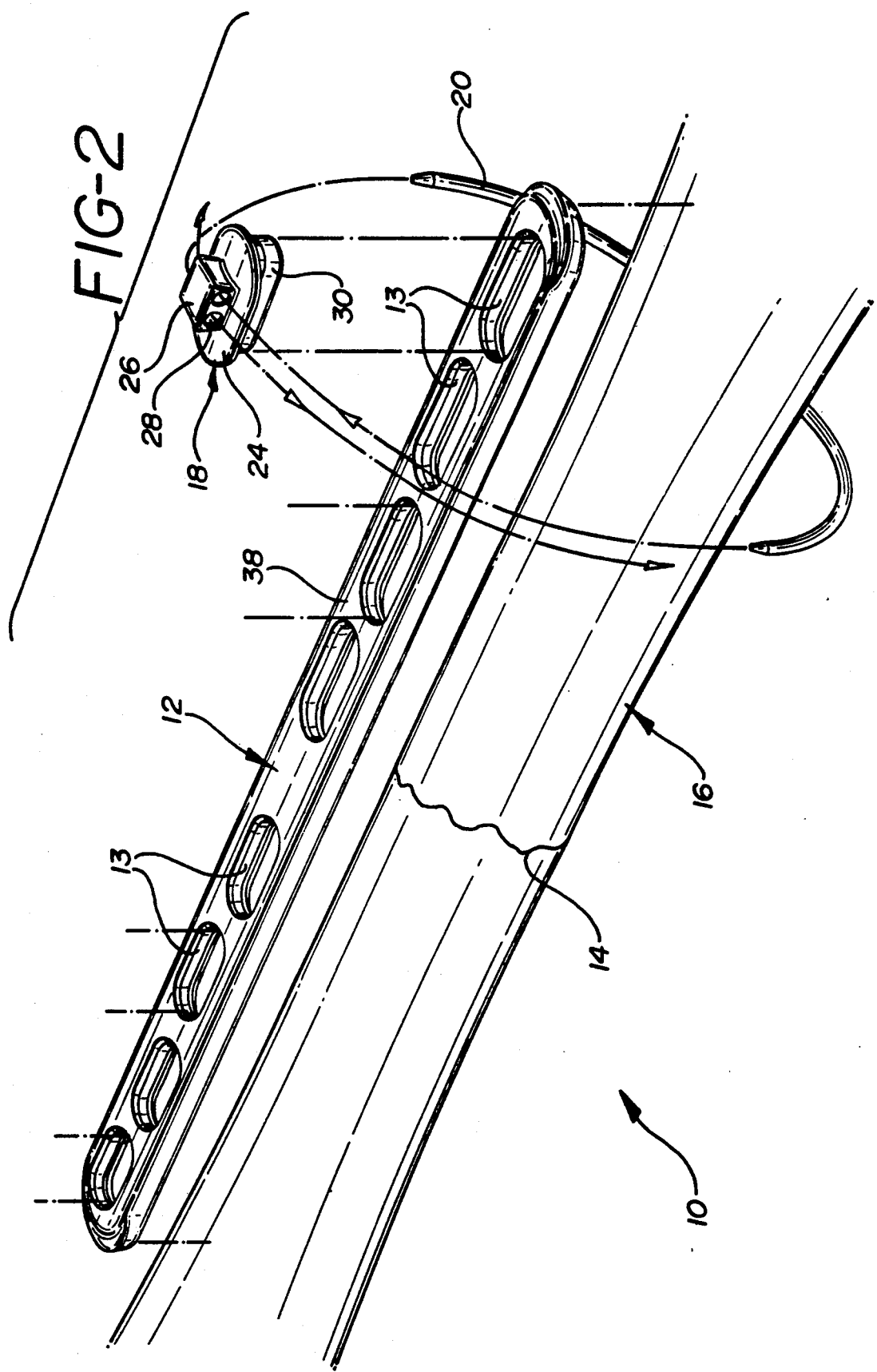

CERCLAGE WIRE POSITIONING INSERT

BACKGROUND OF THE INVENTION

1. Field of the Invention

This invention relates to the field of bone fracture fixation utilizing compression plates. More particularly, it relates to a method of fracture fixation in which cerclage wiring is used in conjunction with bone plates.

2. Description of the Prior Art

In the past, many types of bone plates have been applied to bones, some by screws and others with the help of wire loops. These plates may be of any size or shape, but are usually L-shaped or straight. These plates are placed on the tension side of the non-union (convex side) with the compression plate acting as a tension band which provides dynamic rather than static compression. In the last 20 years bone plates having a self-compressing effect caused by eccentric screw placement was combined with the gliding or sliding effect between the screw head and the plate hole to allow for a greater force transmission within the bone during weight bearing period. Furthermore, due to the spherical configuration of both screw heads and plate holes, the compression instituted initially, is maintained throughout the healing process, even if the screws are not placed at right angles to the plate.

It has also been well known to use wires or cables such as Kirschner wires to fix fractures. Cerclage wiring techniques have been used for fixing long bone fractures, usually in combination with other fixation devices such as bone plates. The wires are passed at a 90° angle to the long axis of the bone in an attempt to prevent slipping in a longitudinal direction and hence loosening.

It is also known in the prior art that when fractures of the femur occur after a prosthetic implant is implanted, that a combination of the use of a bone plate including bone screws in the distal section of a fractured femur may be utilized, but such screws cannot be easily utilized in the proximal section of the fractured femur due to the stem of the implanted, for example, femoral prosthesis. Clearly, for fractures in which the entire medullary canal is filled with a prosthetic stem with or without bone cement, placement of a new internal pin or a new prosthesis with a longer stem is not a viable means of intramedullary fixation.

An alternate method has been used to fix the fracture in which a bone plate is secured by cortical screws in the femur distal to the prosthesis and to secure the plate proximally with the use of cerclage wires. In the past this has required the use of a special bone plate. It is in this situation that the wire or cable positioning insert of the present invention is intended to be used. It has been found that the cerclage wiring around the bone plate tends to migrate longitudinally and can also migrate circumferentially about the bone even after the ends of the wire are clipped together using a standard trochanteric cable crimp sleeve.

By use of the present invention, cerclage wire or cable may be positioned with respect to any desired hole in a bone plate with the positioning insert also acting as a crimp sleeve so that once the wire has been crimped to the positioning insert, longitudinal and circumferential movement is prevented.

In addition, the insert is sized to fit partially within the screw apertures of standard bone plates so that the special bone plates of the prior art are unnecessary.

SUMMARY OF THE INVENTION

It is an object of this invention to provide a wire positioning insert for use with bone plates of the type having a plurality of apertures therein for receiving cortical bone screws.

It is yet another object of the invention to provide a wire positioning insert which has a boss thereon made of malleable metal which can serve as a crimp sleeve and be deformed by a standard cable grip crimping tool.

It is still another object of the invention to provide a wire positioning insert which may be inserted through the aperture of a bone plate and extend outwardly thereof so that such positioning insert may not be lost from the bone plate even should the wire position thereby fail.

These and other objects of the present invention are achieved in the present invention by a cable positioning insert for use with a bone plate of the type having a series of apertures therein for receiving bone screws. The bone plate is normally positioned across a fracture in a long bone with bone screws being screwed through the aperture into the bone to stabilize and compress the fracture.

The cable positioning insert has a body shape for at least partial insertion into at least one of the apertures in the bone plate. The body further includes a flange extending from the body for engaging either the surface of the bone plate adjacent the bone or the surface of the bone plate facing outwardly of the bone. In either case, a boss extends through the aperture and outwardly of the body in a direction away from the bone when the bone plate is mounted thereon. The boss has at least one opening and preferably two openings therein for accommodating the cerclage wire or cable and positioning it relative to the aperture and the outer surface of the bone plate. The openings may be in the form of a generally cylindrical bore through the boss.

In the embodiment wherein the positioning insert has a flange engaging the underside of the bone plate, the boss extends from the flange surface through the at least one aperture a sufficient distance for positioning the openings outwardly of the outer surface of the bone plate. This allows the cerclage wire to be positioned generally flush with the outwardly facing surface of the bone plate. Since the cerclage wire must be crimped in place, it has been found advantageous to make the boss of the insert out of a malleable material so that it can be deformed under pressure with a crimp tool to flatten the generally cylindrical bore and to capture the cable therein.

These and other objects and advantages of the present invention will become apparent from the following description of the accompanying drawings, which disclose two embodiments of the invention. It is to be understood that the drawings are to be used for the purpose of illustration only, and not as a definition of the invention.

BRIEF DESCRIPTION OF THE DRAWINGS

In the drawings, wherein similar reference characters denote similar elements throughout the several views:

FIG. 1 is an isometric view of the bone fracture stabilization apparatus including the positioning insert of the present invention;

FIG. 2 is an exploded view of the bone fracture stabilization apparatus of the present invention prior to being placed upon a long bone;

DESCRIPTION OF THE PREFERRED EMBODIMENT

Figure 1A:
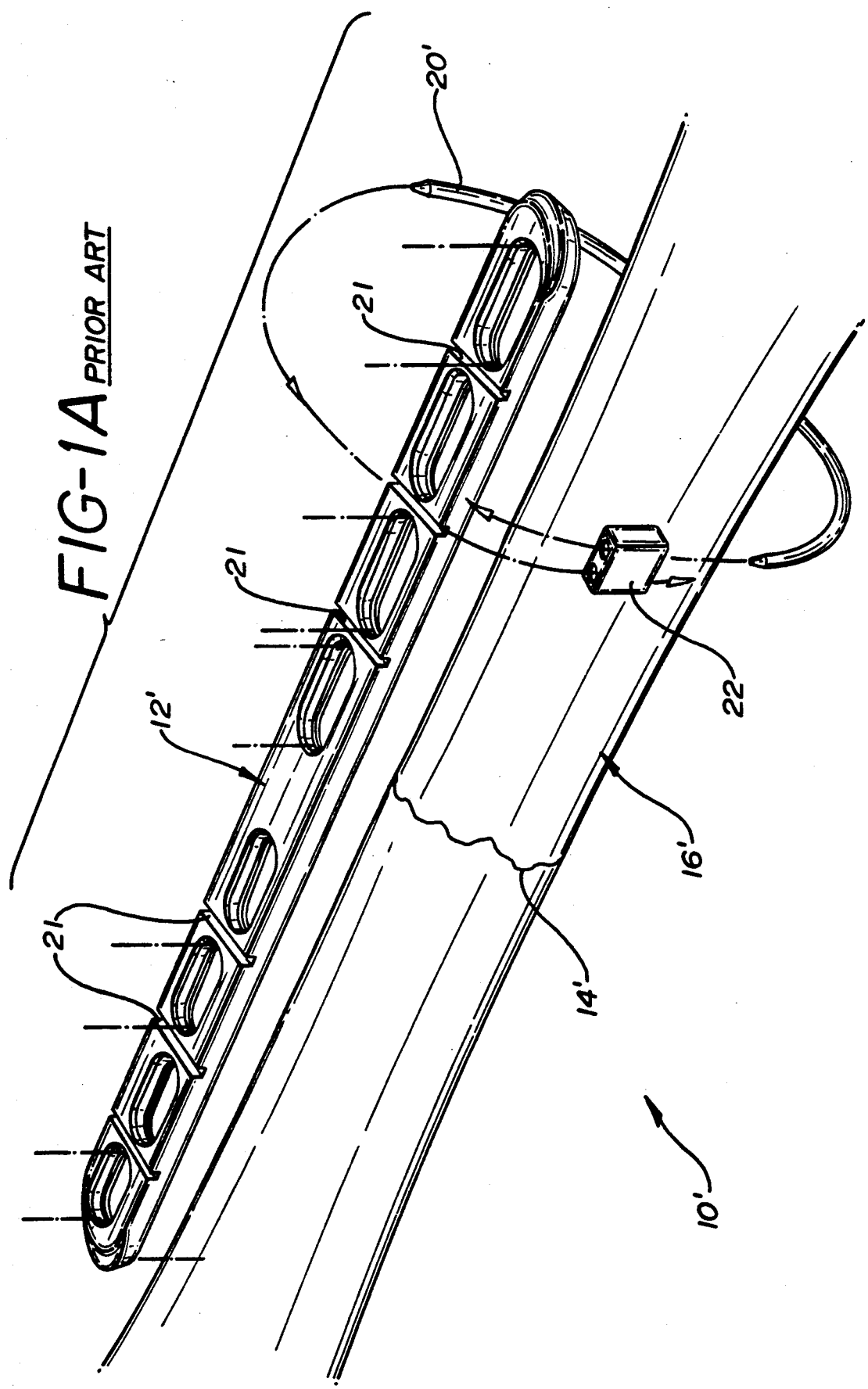
FIG. 1A is an isometric view of the prior art fracture stabilization apparatus using cerclage wiring.
Figure 3:
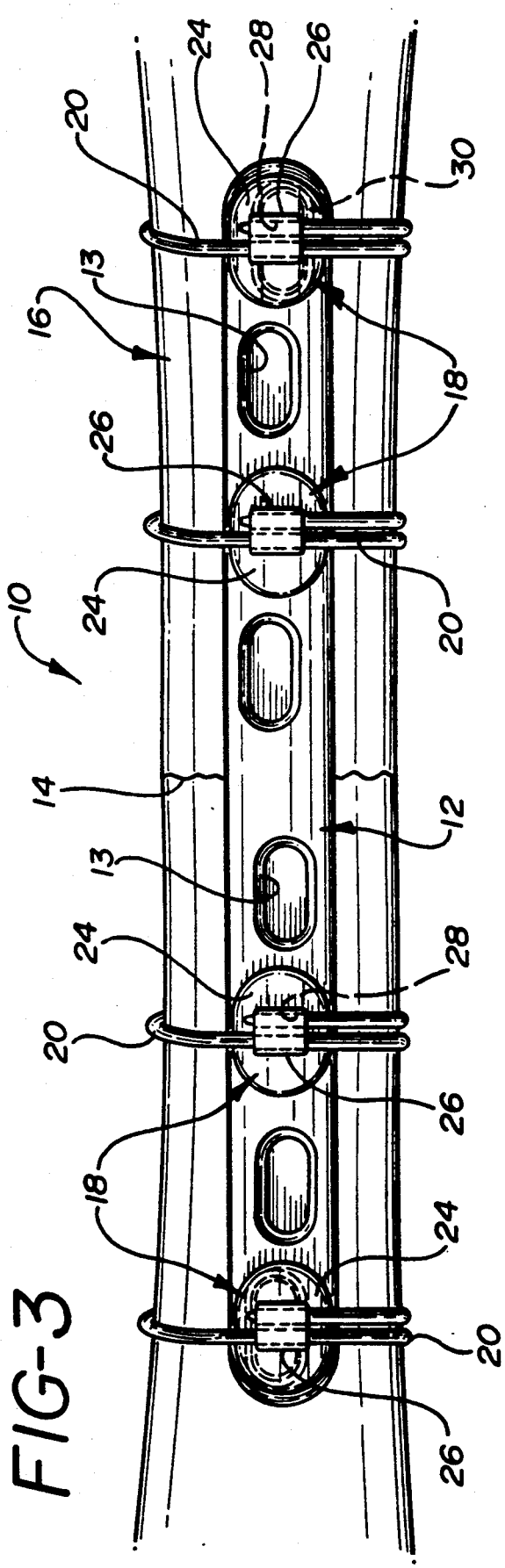
FIG. 3 is a plan view of the bone fracture stabilization apparatus of FIG. 2 after attachment to fracture site.
Figure 4:
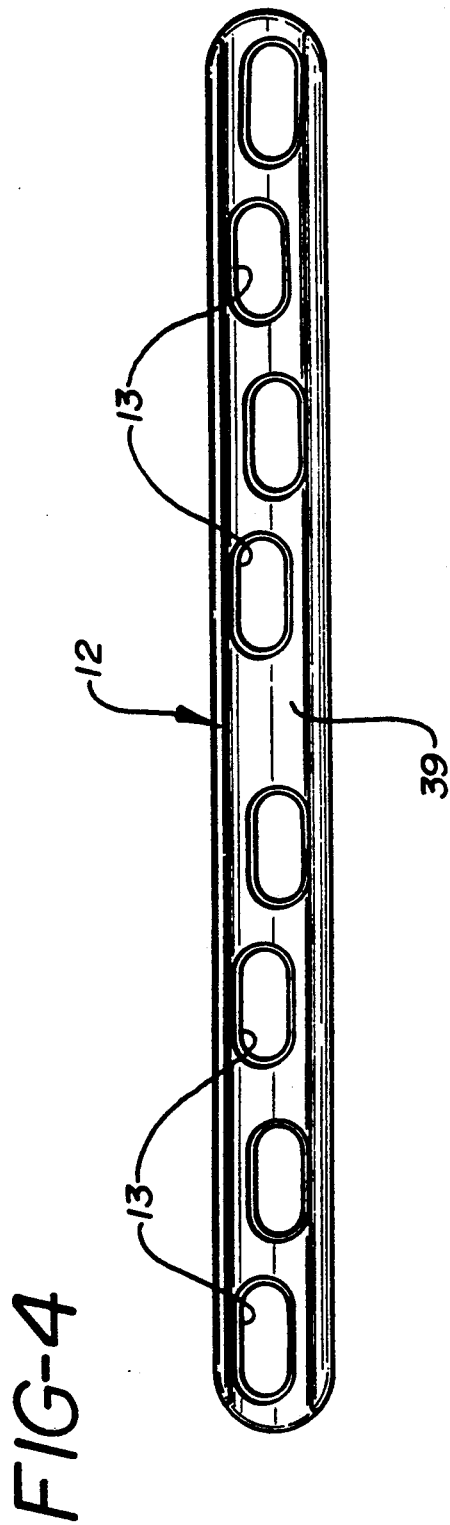
FIG. 4 is a plan view of a bone plate capable of being utilized with the present invention.

Referring to FIG. 1 there is shown the bone fracture stabilization apparatus of the present invention, generally denoted as 10. A bone plate 12 having a series of apertures 13 is secured across a fracture site 14 of a long bone 16 by use of the wire positioning insert 18 of the present invention. A wire or cable 20 is wrapped around bone plate 12 and bone 16 and crimped in position in a manner hereinafter described.

Positioning insert 18 of the present invention includes a flange 24 with a boss 26 extending therefrom outwardly of bone 16. Boss 26 includes a pair of generally cylindrical bore-like openings 28 extending therethrough in a direction generally perpendicular to the long axis of bone 16. Referring to FIG. 1A, there is shown a fracture fixation apparatus used in the prior art for use with cerclage wiring generally denoted as 10'. In this apparatus, a special grooved bone plate 12' would be positioned over fracture site 14' on long bone 16' and held in position by a wire or cable 20' which is held in position by grooves 21 formed on the outer surface of bone plate 16. A crimp sleeve 22 is then used to lock the wire around the bone plate 12' and bone 16'. As can be seen, the grooves 21 of the prior art bone plate 12' do not prevent the circumferential migration of cerclage wire 20'.

Figure 5:
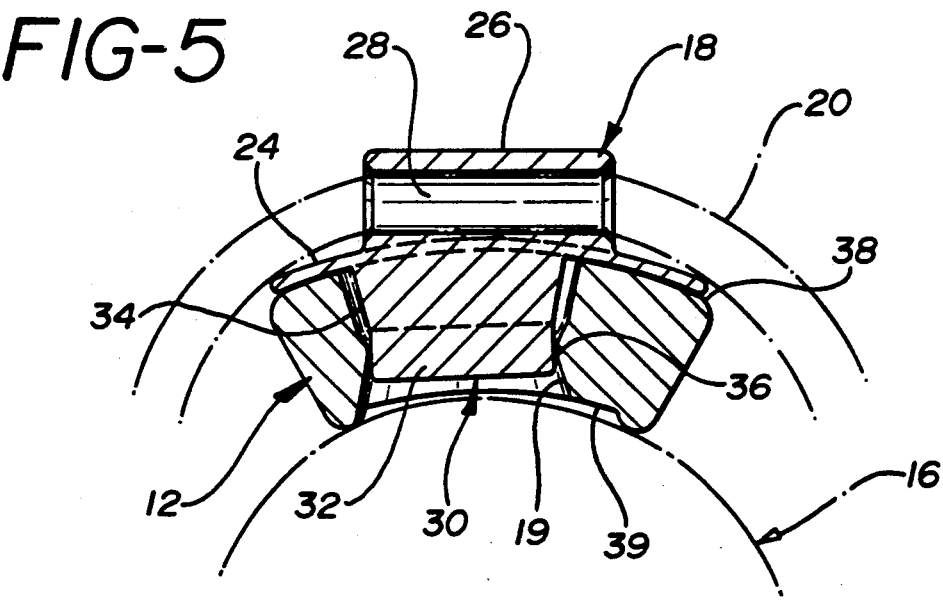
FIG. 5 is cross-sectional view of the bone fracture stabilization system shown in FIG. 1 along line 5—5.
Figure 6:
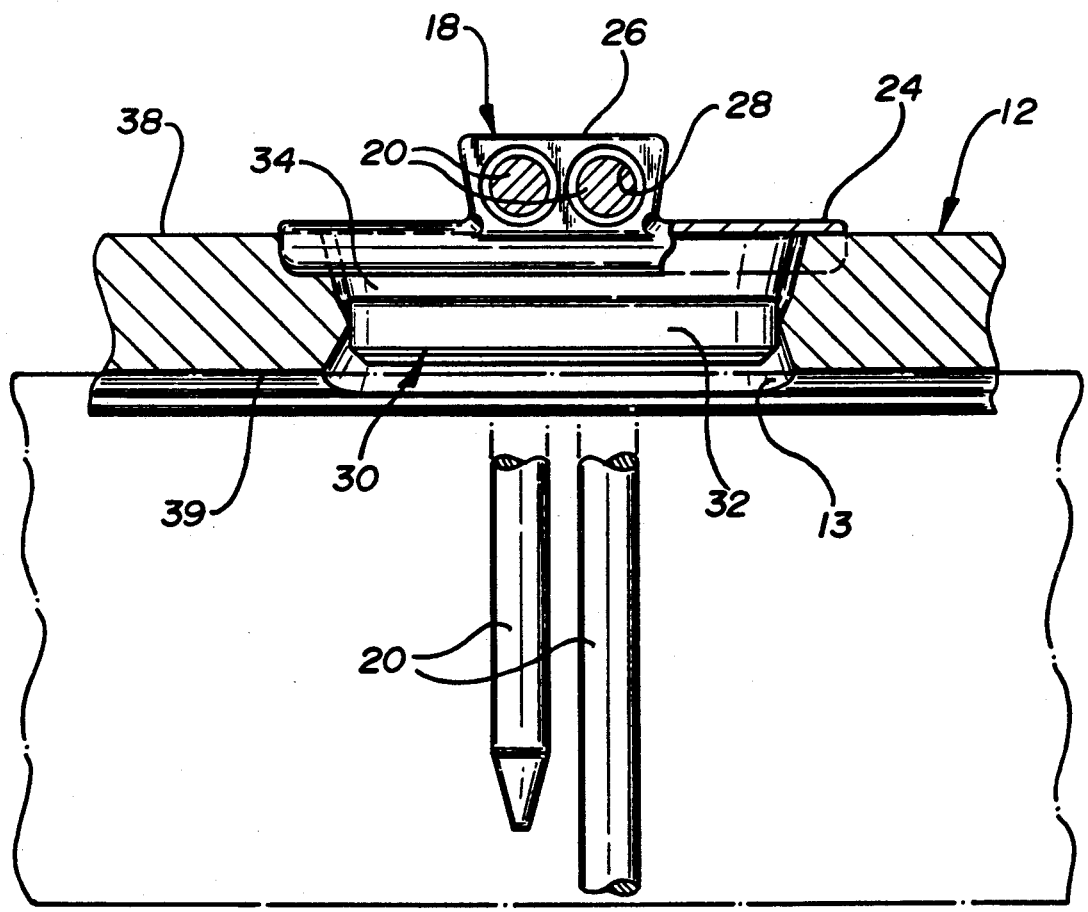
FIG. 6 is an elevation view, partially in cross-section, of the bone fracture stabilization apparatus shown in FIG. 1 with the cross-sectional view taken along line 6—6.

Referring to FIGS. 2 through 6, there is shown the geometry of positioning insert 18 of the present invention. In addition to flange 24 and boss 26, the insert includes positioning extension 30 which extends from flange 24 and has a shape generally conforming to aperture 13 in bone plate 12. As can be seen in FIG. 5, extension 30, in cross-section, is composed of a lower section 32 and an upper section 34. Section 34 tapers inwardly to generally conform with the cross-section of apertures 13 with section 32 tapering slightly outwardly to engage an area 36 of aperture 13 which has a reduced diameter. The reduced diameter 36 normally provides a seat for the head of a bone screw (not shown). As can be further seen in FIG. 5, in the preferred embodiment boss 26, which contains at least one opening 28, is centered with respect to the outer surface 38 of bone plate 12 and not necessarily to the centerline of aperture 13 in the bone plate. This is done because the apertures 13 of many bone plates 12 are staggered with respect to the centerline of the bone plate. This is done so that the bone screws go into the bone staggered with respect to the centerline thereof to minimize the possibility of bone 16 splitting. Thus, the holding forces generated by the cable 20 after the crimping step described below act through the longitudinal centerline of bone plate 12 in a radial direction.

In the preferred embodiment, at least boss 26 of positioning insert 18 is made of a material soft enough to be deformed by a standard crimping tool (not shown). It has been found that cobalt chrome molydenium alloy (such as Vitallium) or stainless steel is a suitable material for making the entire positioning insert 28 and provides the malleability required for boss 26 such that generally cylindrical bores therein may be flattened to an elliptical shape and thereby lock wire 20 in position as is well known in the wire crimping art.

Positioning insert 18 of the present invention may be utilized with any bone plate, whether straight or L-shaped. Generally, apertures 13 of a wide variety of bone plates may be made identical in size and therefore positioning inserts 18 may be made available to the surgeons so that if a decision is made not to attach bone plate 12 to bone 16 with bone screws, cerclage wire 20 may be easily utilized with standard, non-grooved bone plates. To accomplish this a surgeon merely inserts extension portion 30 into aperture 13 so that flange 24 either engages upper surface 38 of bone plate 12 or under surface 39 (not shown) of bone plate 12 with boss 26 extending sufficiently outwardly of the bone so that generally cylindrical openings 28 are positioned outwardly of surface 38 of bone plate 12. The surgeon inserts wire 20 and tensions it. The surgeon then may either deform boss 26 to flatten generally cylindrical bores 28, thereby capturing the wire with respect to insert 18 or in the alternative, can use a crimp sleeve 22 to lock the wire in position after sufficient tensioning.

Figure 7:
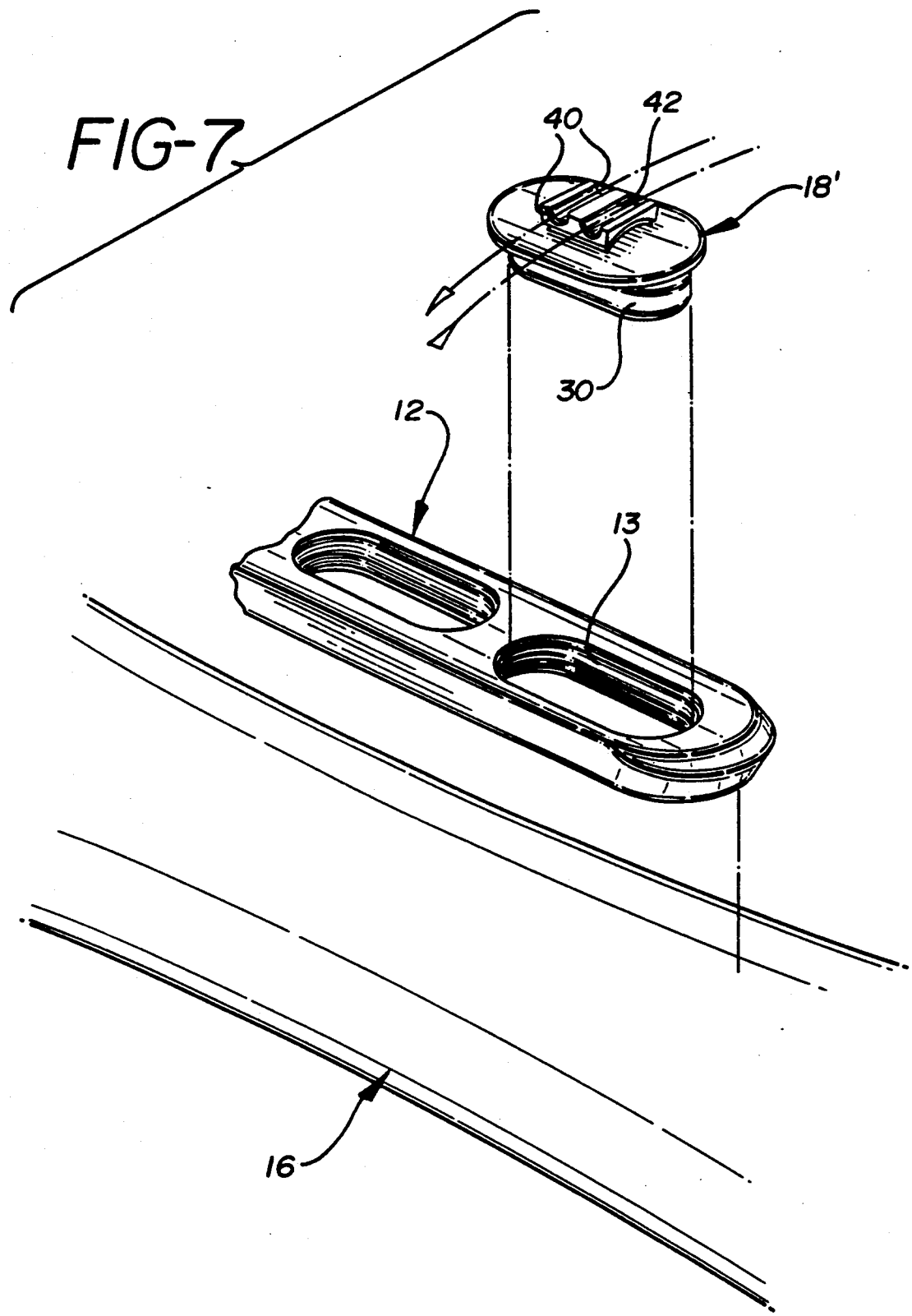
FIG. 7 is a partial isometric view of an alternate embodiment of the wire positioning insert of the present invention.
Figure 8:
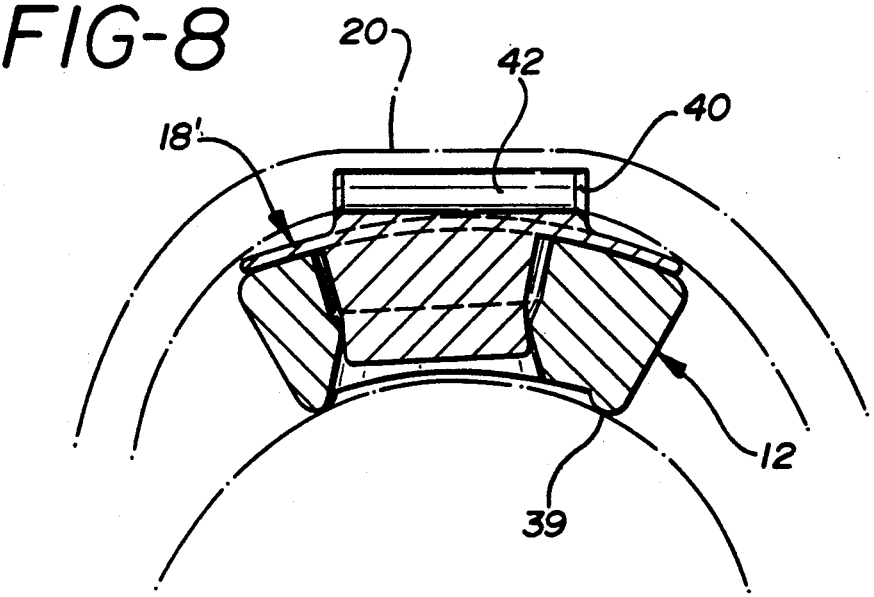
FIG. 8 is a cross-sectional view similar to that shown in FIG. 5 but utilizing the positioning insert embodiment shown in FIG. 7.
Figure 9:
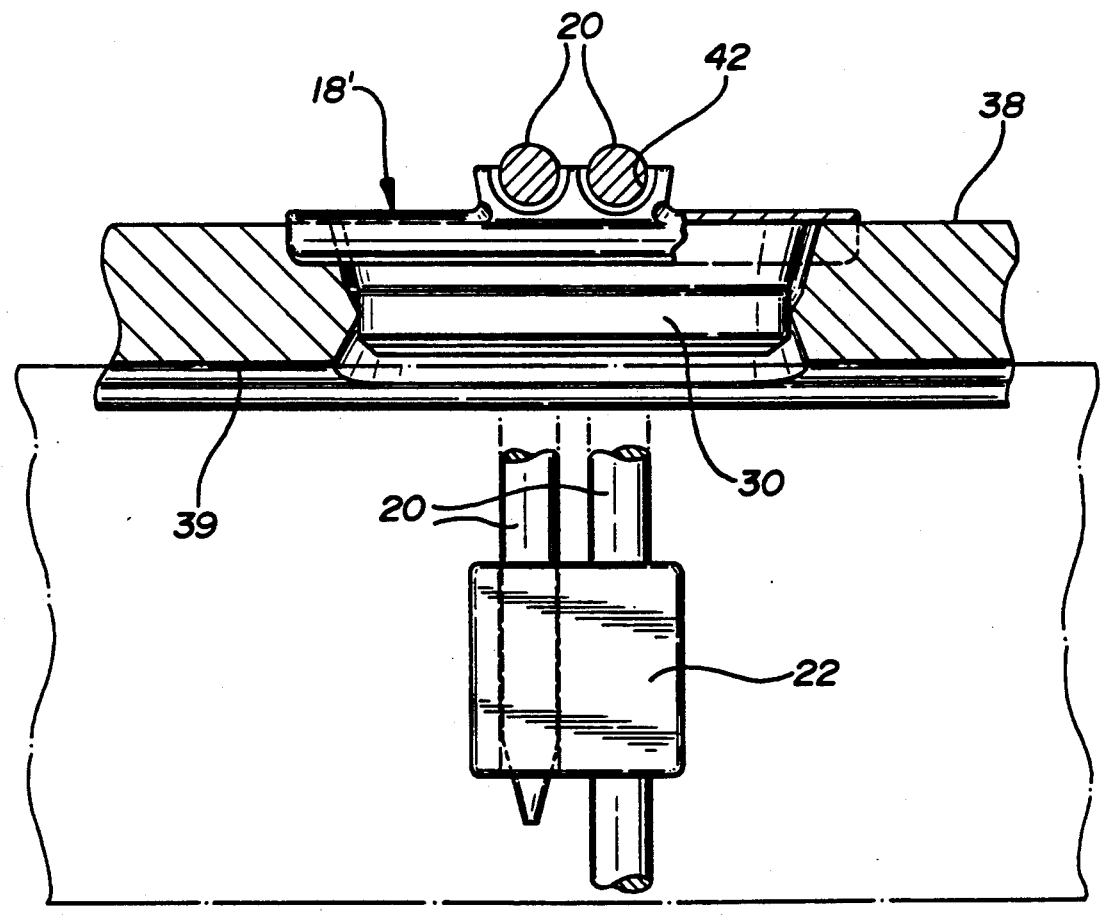
FIG. 9 is an elevation view, partially in cross-section, similar to that shown in FIG. 6 but utilizing the positioning insert of FIG. 7.

Referring to FIGS. 7-9, there is shown an alternate embodiment of the present invention in which a positioning insert generally denoted as 18' is utilized within aperture 13 of bone plate 12. The positioning insert 18' is in all respects similar to positioning insert 18 with the exception that boss 26 is replaced by a boss 40 which has at least one and preferably a pair of open circular grooves 42 formed therein. Wire 20 is then wrapped around the bone plate after insertion of positioning insert 18' and placed with grooves 42 for positioning the wire relative to bone plate 12. The wire is locked in position by a crimp element 22 which is deformed about one end of the wire and the adjacent wire wrap.

While two examples of the present invention have been described, it is obvious that many changes and modifications may be made thereunto without departing from the spirit and scope of the invention.

We claim:

1. A bone fracture stabilization apparatus comprising:
   at elongated bone plate having a plurality of apertures in the form of an elongated slot with rounded ends extending through said bone plate;
   at least one insert having a body shaped for insertion into at least one of said plurality of apertures in said bone plate, said body having a flange extending from said body for engaging an outer surface of said bone plate and a boss extending from said body in a direction away from the fractured bone, said boss having at least one opening therein;

a cable extending through said opening in said boss and around the fractured bone; and a means for fixing the length of cable after said cable has been tensioned around the bone to hold the bone plate in engagement with the fractured bone.

2. The bone fracture stabilization apparatus as set forth in claim 1 wherein said opening in said boss comprises a pair of generally cylindrical shaped openings with the longitudinal axis of said openings extending generally perpendicular to the long axis of the fractured bone.

3. The cable positioning insert as forth in claim 2 wherein said boss is made of a malleable material that deforms under pressure to flatten said generally cylindrical openings and capture said cable therein.

4. The bone fracture stabilization apparatus as set forth in claim 3 wherein said means for fixing the length of said cable is crimping said boss to flatten said generally cylindrical openings therein and fix the cable in position with respect to said bone plate.

5. The bone fracture stabilization apparatus as set forth in claim 1 wherein said opening in said boss comprises a pair of generally semicircular outwardly open grooves.

6. The bone fracture stabilization apparatus as set forth in claim 5 wherein said means for fixing the length of said cable is a sleeve crimped to two coils of said cable.

7. The cable positioning insert as set forth in claim 1 wherein said flange engages a surface of said bone plate adjacent the outer surface of a bone on which the bone plate is mounted.

8. The cable positioning device as set forth in claim 7 wherein said boss extends from said flange through said at least one aperture a sufficient distance to position said at least one opening outwardly of outer surface of the bone plate.

9. A bone fracture fixation system comprising:

a bone plate of the type having a plurality of apertures therein of predetermined shape spaced along the length of the bone plate for accommodating a head of a bone a one-piece insert having a body generally corresponding in shape to the predetermined shape of said apertures in said bone plate for partial insertion therein, said body having a flange for engaging a surface of said bone plate;

a cable for engaging said insert; and a boss extending from said flange in a direction away from the bone when the bone plate is mounted thereon, said boss having at least one opening therein for accommodating the cable and positioning it along the length of the bone plate, said boss extending a sufficient distance to position said at least one opening therein outwardly of an outer surface of the bone plate.

10. The fracture fixation system as set forth in claim 9 wherein said boss has two opening therein for receiving said cable.

11. The fracture fixation system as set forth in claim 10 wherein said opening in said boss are generally cylindrical in cross-section with a diameter larger then a corresponding diameter of said cable.

12. The fracture fixation system as set forth in claim 11 wherein said boss is made of a malleable material that deforms under pressure to flatten said generally cylindrical openings and capture said cable therein.

13. The fracture fixation system as set forth in claim 10 wherein said two openings in said boss are in the form of generally semi-circular grooves formed in the outer surface of said boss.

* * * * *